United States Patent [19]
Lindberg et al.

[11] 3,976,771
[45] Aug. 24, 1976

[54] GLYCYLGLYCINE AMIDE PREPARATIONS AND METHOD OF USE ANTIARRHYTHMIC

[75] Inventors: Ulf Hendrik Anders Lindberg; Sven Bengt Arvid Akerman, both of Sodertalje, Sweden

[73] Assignee: Astra Lakemedel Aktiebolag, Sodertalje, Sweden

[22] Filed: June 13, 1975

[21] Appl. No.: 586,636

Related U.S. Application Data

[62] Division of Ser. No. 331,899, Feb. 12, 1973, Pat. No. 3,910,871.

[30] Foreign Application Priority Data

Feb. 15, 1972 United Kingdom................. 6943/72

[52] U.S. Cl. ............................................... 424/177
[51] Int. Cl.² ........................................ A61K 37/00
[58] Field of Search................... 424/177; 260/112.5

[56] References Cited
OTHER PUBLICATIONS

Koelzer et al.: Arzneimittelforschung, 9 (1952), pp. 167–175.
Pfeiffer et al.: Journal Fur Praktische Chemie, vol. 157, pp. 123–124 (1941).

Primary Examiner—Lewis Gotts
Assistant Examiner—Dolph H. Torrence
Attorney, Agent, or Firm—Brumbaugh, Graves, Donohue & Raymond

[57] ABSTRACT

A novel class of glycylglycine amides has been discovered having value as antiarrhythmic agents. The preferred compound of the present invention has the structural formula

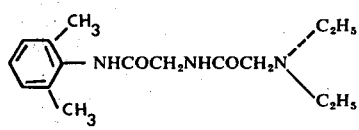

Also included within the scope of this invention are compounds having $C_1$–$C_3$ alkyl, alkoxy and halo substituents in the ortho, para or meta positions of the aromatic ring, compounds in which the phenyl group is replaced by benzyl or substituted benzyl and compounds in which the glycylglycine chain may be substituted with lower alkyl groups or may contain heterocyclic rings.

18 Claims, No Drawings

GLYCYLGLYCINE AMIDE PREPARATIONS AND METHOD OF USE ANTIARRHYTHMIC

This is a division of our copending application Ser. No. 331,899 filed Feb. 12, 1973 now U.S. Pat. No. 3,910,871.

The present invention relates to new, therapeutically active compounds, to processes for their preparation; to pharmaceutical preparations containing them; and to their use in medicine. The invention also relates to new chemical intermediates which are useful in preparing the new, therapeutically active compounds.

More particularly, the present invention relates to novel compounds with antiarrhythmic properties and to their use for suppressing cardiac arrhythmias in mammals.

The introduction of intensive coronary care has renewed emphasis in the treatment of ventricular extrasystoles and other cardiac arrhythmias in mammals. At the present time, there is no drug which is completely satisfactory for the long-term control of arrhythmias. Conventional drugs, such as quinidine, procainamide, propanolol and diphenylhydantoin (phenytoin /Brit.Pharm./) have all exhibited undesirable side effects. It is particularly desirable to diminish the incidence of side effects such as decreased contractility of the heart, hypotension, and convulsions. Other important objectives are to provide improved longevity of action and improved activity especially by the oral route.

The use of 1-(2′, 6′-dimethyl-phenoxy)-2-aminopropane has also been studied. Its action on the central nervous system is similar to that of phenytoin. *The British Journal Of Pharmacology*, Vol. 39, pp. 183P -184P (1970). Xylocain (lidocaine), whose chemical name is 2-diethylamino-2′, 6′-acetoxylidide, is a local anesthetic which also has been used intravenously and intramuscularly as an antiarrhythmic drug, Parkinson et al. *Brit. Med. J.*, Vol. 2, pp. 29–30 (1970) and *The Merck Index*, 8th Edition, (Merck & Co., Inc., Rahway, New Jersey, 1968) p. 618, but which is not orally effective due to low levels of the drug in the blood. Eisinger and Hellier, *Lancet* 1969, *II*, 1303 and Boyes et al., *Clin. Pharmacol. Therap.* 12 No. 1, pp. 105–116 (1971). When lidocaine is administered orally there is a pronounced loss of the drug probably due to the function of the liver, through which most of the drug has to pass immediately following absorption from the intestinal tract. The duration of these blood levels obtained with lidocaine is also fairly short thereby precluding long duration of protection.

Another class of known drugs which exhibit antiarrhythmic properties are the 2-amino tetralins as described by D. M. Graeff in *Journal of Medicinal Chemistry*, Vol. 14 (1), pp. 60–62 (1971).

Certain local anesthetics have been described in Arzneinittelforschung, 9 (1952) pp. 167–175. Among them is the compound

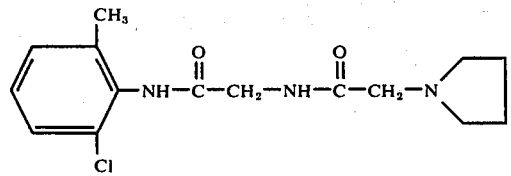

However, its use as an antiarryhthmic agent is not suggested.

According to the present invention, it has been discovered that compounds of the class:

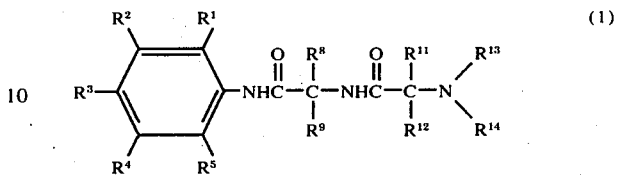

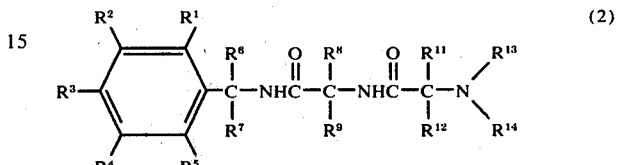

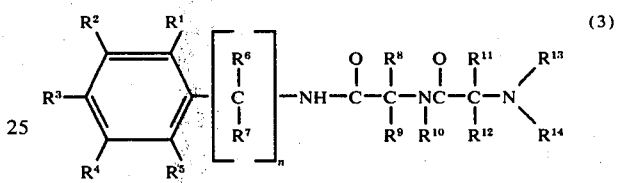

and therapeutically acceptable salts thereof have valuable antiarrhythmic properties. In the foregoing formulas $R^1$, $R^2$, $R^3$, $R^4$ and $R^5$ are the same or different and selected from the class consisting of hydrogen, halogen, alkyl groups having from 1 to 3 carbon atoms and alkoxy groups having from 1 to 3 carbon atoms, and $R^6$, $R^7$, $R^8$, $R^9$, $R^{11}$, $R^{12}$, $R^{13}$ and $R^{14}$ are the same or different and selected from the group consisting of hydrogen and alkyl groups having from 1 to 3 carbon atoms; and in Formula 3, $n$ is 0 or 1, $R^{10}$ is hydrogen or linked with $R^9$ to form a 5 to 6 membered nitrogen containing heterocyclic ring and $R^{13}$ and $R^{14}$ are selected from the class consisting of hydrogen and alkyl groups containing from 1 to 3 carbon atoms, or are joined to form a heterocyclic, nitrogen containing, 4 to 6 membered ring; or $R^{14}$ is linked with $R^{12}$ to a heterocyclic nitrogen containing 5 or 6 membered ring, provided that in Formula 3 there is present at least one heterocyclic ring and provided that in Formula 3 $R^1$ through $R^5$ do not include halogen when $R^{13}$ and $R^{14}$ form a heterocyclic ring.

Preferred subclasses of compounds within the foregoing class are those in which the extent of substitution is limited. These preferred subclasses are:

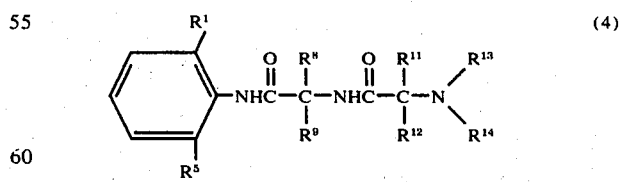

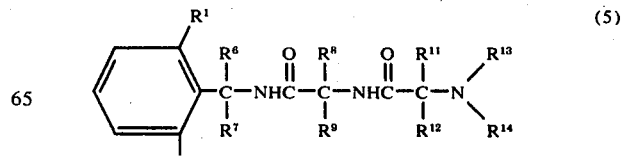

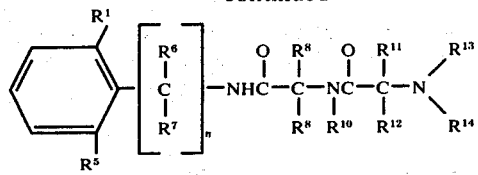 (6)

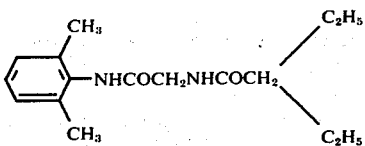

wherein $R^1$, $R^5$, $R^6$, $R^7$, $R^8$, $R^9$, $R^{10}$, $R^{11}$, $R^{12}$, $R^{13}$, $R^{14}$, and $n$ are as defined above, and the radicals $R^6$, $R^7$, $R^8$, $R^9$, $R^{11}$, $R^{12}$, $R^{13}$, and $R^{14}$ do not contain a total of more than eight carbon atoms. In formulas 4 and 5, there are no heterocyclic rings, while in formula 6, $R^9$, $R^{10}$, $R^{12}$, $R^{13}$ and $R^{14}$ may form heterocyclic rings as in formula 3.

Illustrative examples of the radicals contained in formula 1 and 2 are:

$R^1$, $R^2$, $R^3$, $R^4$ and $R^5$:
H, $-CH_3$, $-C_2H_5$, $-(CH_2)_2CH_3$, $-CH(CH_3)_2$, $-OCH_3$, $-OC_2H_5$, $-O(CH_2)_2CH_3$, $-OCH(CH_3)_2$, Cl, Br.

$R^6$, $R^7$, $R^8$, $R^9$, $R^{11}$, $R^{12}$:
H, $-CH_3$, $C_2H_5$, $-(CH_2)_2CH_3$, $-CH(CH_3)_2$.

$R^{13}$, $R^{14}$:
H, $-CH_3$, $-C_2H_5$, $-(CH_2)_2CH_3$, $-CH(CH_3)_2$.

Ilustrative examples of heterocycles in formulas 3 and 6 included in the scope of

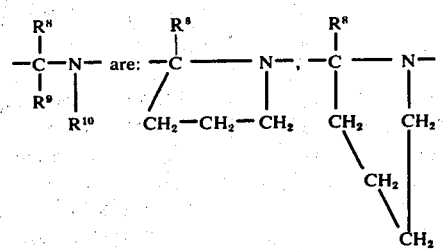

Illustrative examples of heterocycles in Formulas 3 and 6 included in the scope of

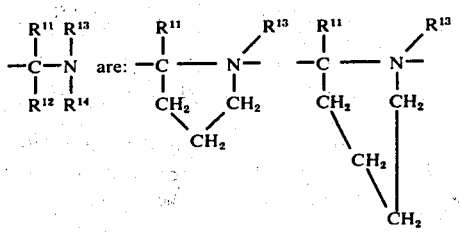

Illustrative examples of heterocycles in Formulas 3 and 6 included in the scope of

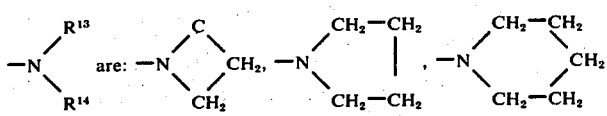

The preferred compound of the invention is the compound of the structural formula When the compounds according to the invention are required in the form of a therapeutically acceptable salt, such a salt may be formed by converting the normal base form into the desired salt by reacting it with the appropriate acid. The expression "therapeutically acceptable salt" is recognized in the art to designate an acid addition salt which is physiologically innocuous when administered in a dosage and at an interval (e.g. frequency of administration) that is effective for the indicated therapeutic use of the parent compound. Typical therapeutically acceptable acid addition salts of the compounds of the present invention include, but are not limited to, the salts of mineral acids, such as hydrochloric, phosphoric and sulfuric acid, and the salts of organic acids, such as succinic and tartaric acid, and sulphonic acids.

The duration of the antiarrhythmic effect exhibited by compounds according to the invention is longer than the antiarrhythmic effect of lidocaine, and additionally, compounds of the invention have an acute toxicity which is lower than the acute toxicity of lidocaine. The fact that these improvements are shown when orally administered is of particular significance. Moreover, the compounds of the present invention appear not to effect the contractility of the heart adversely and seem to have only a slight effect on the blood pressure.

In clinical practice the compounds of the invention will normally be administered orally or by injection in the form of pharmaceutical preparations comprising the active ingredient in the form of the free base or one of the common therapeutically acceptable salts, e.g. the hydrochloride, in association with a pharmaceutically acceptable carrier which may be a solid, semi-solid or liquid diluent or an ingestible capsule. Usually the active substance will comprise between 0.1 and 10% by weight of the preparation as, for example, in a water solution in the form of its soluble acid salt. When solid preparations, e.g. tablets or capsules, are used the amount of the claimed compound can be much higher. A concentration of 100% by weight in such preparations could be used.

To produce pharmaceutical preparations in the form of dosage units of 100–250 mg each for oral application containing a compound of the invention in the form of the free base or a pharmaceutically acceptable acid addition salt, such a compound may be mixed with a solid, pulverulent carrier, for example, lactose, saccharose, sorbitol, mannitol, starches, such as potato starch, corn starch or amylopectin, cellulose derivatives, and gelatin. The carrier may also be a lubricant, such as magnesium or calcium stearate, a Carbowax or other polyethylene glycol wax compressed to form tablets, or preferably, cores which are then coated with a concentrated sugar solution which may contain, e.g., gum arabic, gelatin, talcum and/or titanium dioxide, or alternatively with a lacquer dissolved in a readily volatile organic solvent or mixture of organic solvents. Dyestuffs can be added to these coatings. Sustained release tablets are obtained by using several layers of the active drug, separated by slowly-dissolving coatings. Another way of preparing sustained release tablets is to divide the dose of the active drug into the granules with coatings of different thickness, and compress the granules into tables together with the carrier substance. The active substance can also be incorporated in slowly-dissolving tablets made, for example, of fat and wax substance, such as a physiologically inert plastic substance as disclosed in the Fryklof U.S. Pat. No. 3,317,394.

Soft gelatin capsules (pearl-shaped, closed capsules) and other closed capsules consist, for example, of a mixture of gelatin and glycerol, and contain, e.g., mixtures of the active substance with a vegetable oil, and hard gelatin capsules contain granulates of the active substance with solid, pulverulent carriers such as lactose, saccharose, sorbitol, and mannitol, starches such as potato starch, corn starch or amylopectin, cellulose derivatives or gelatin, as well as magnesium stearate or stearic acid.

For parenteral application by injection the preparations of the invention advantageously comprise an aqueous solution of a water-soluble, pharmaceutically acceptable salt of the active substance and optionally also a stabilizing agent and/or a buffer substance. The solutions may be made isotonic by the addition of such substances as sodium chloride.

The compounds according to the present invention may be prepared by methods which are known per se.

Thus compounds of the formulas 1-6 wherein the radicals

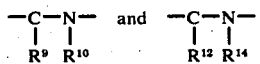

both may form heterocyclic nitrogen-containing groups may be prepared by

A. reacting a compound of the formula

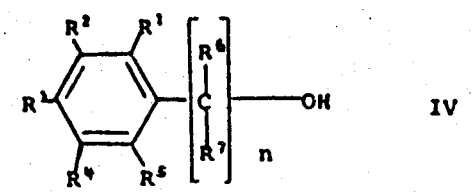

wherein $n$ and $R^1-R^7$ have the meaning specified above, with a compound of the formula

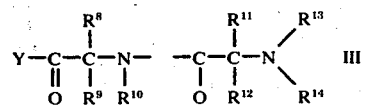

wherein $R^8-R^{14}$ have the meaning specified above and wherein Y is a radical selected from the class consisting of hydroxy, halogen such as Cl and Br, and functionally equivalent rests such as p-toluenesulphonyl;

B. reacting a compound of the formula

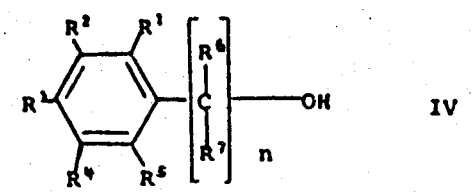

wherein $n$ and $R^1-R^7$ have the meaning specified above, with a compound of the formula

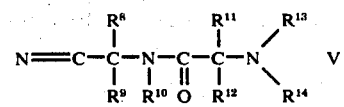

wherein $R^8-R^{14}$ have the meaning specified above.

The reaction B is suitably carried out in strongly acidic media, e.g. concentrated sulphuric acid, benzenesulphonic acid, etc.

Compounds of the Formula 3 wherein the radical

but not the radical

may form a
heterocyclic nitrogen containing ring may be prepared by

C. reacting a compound of the formula

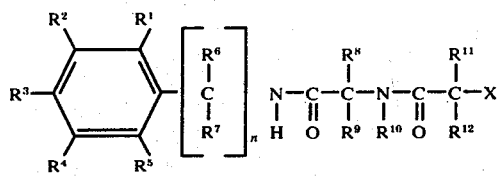

VI wherein $n$ and $R^1$–$R^{12}$ have the meaning specified above and wherein X is selected from the group consisting of halogen, such as Cl or Br, and functionally equivalent groups such as

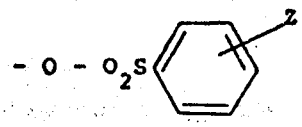

wherein Z is selected from the group consisting of hydrogen and alkyl groups containing not more than 4 carbon atoms, with a compound of the formula

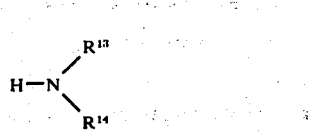

VII wherein $R^{13}$ and $R^{14}$ have the meaning specified above.

When the radical Y in Method A is a hydroxy group, the reaction is suitably carried out in presence of a coupling agent such as dicyclohexylcarbodiimide.

Compounds of the formula VI which do not contain any heterocyclic groups may be prepared according to the following reaction schema. The designation Ar in the formula means

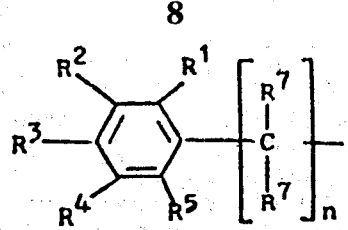

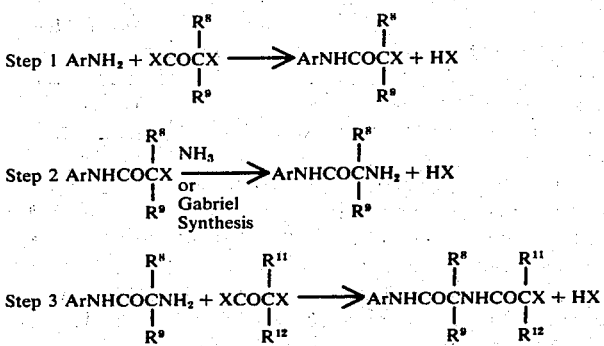

The radicals $R^8$–$R^{12}$ have the meaning specified above. The radical X is halogen such as Cl and Br.

Compounds of the formula VI wherein the grouping

may designate a heterocyclic nitrogen-containing ring may be prepared according to the following reaction schema. The designation Ar in the formula means

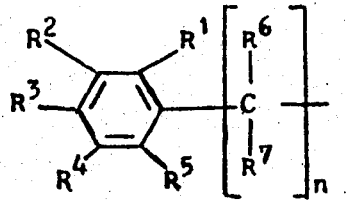

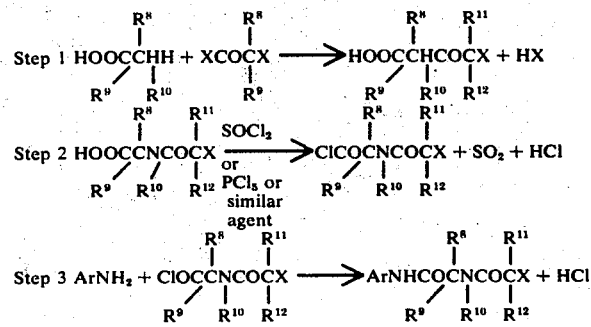

The chemical intermediates with the structural formula

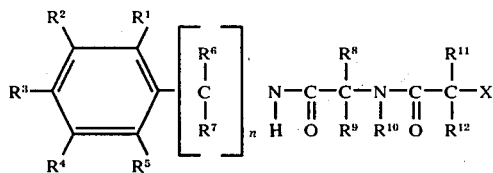

VI wherein $n$, $R^1$-$R^{12}$ and X have the meaning specified above, constitute a further aspect of the present invention and are included within the scope thereof. Compounds of the formula VI wherein X is Cl are particularly useful as intermediates.

Compounds according to Formulas 1-6, wherein $R^{13}$=$R^{14}$=H can also be prepared by the following general procedure:

D. reacting a compound of the formula

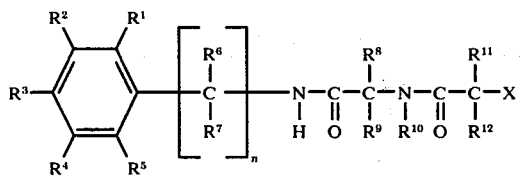

wherein $n$ and $R^1$-$R^{12}$ have the meaning specified before and wherein X is selected from the group consisting of halogen, such as Cl and Br, with potassium phthalimide of the formula

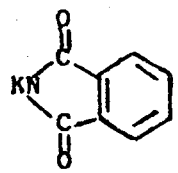

forming an intermediate of the structure

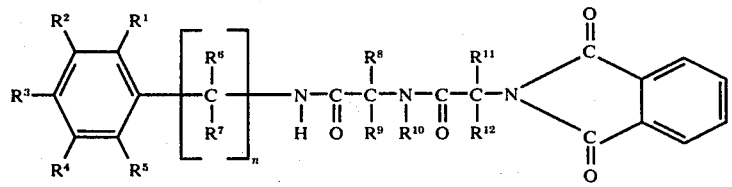

which subsequently, with or without isolation, by means of reaction with 1. hydrazine hydrate, $H_2NNH_2 \cdot H_2O$ and
2. hydrochloric acid is transferred to the desired compound

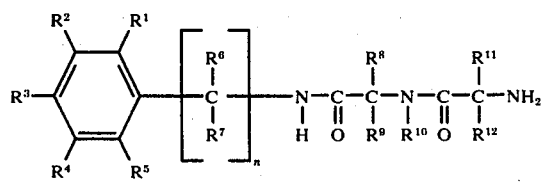

wherein $n$ and $R^1$-$R^{12}$ have the meaning specified above.

It will be appreciated that certain of the compounds according to the present invention exist in the form of optically active isomers, which may be isolated in any principally known way for resolution of an amine, and it is understood that such a manner will be included within the scope of the present invention. The racements obtained at the above reactions can be resolved into the enantiomers by converting the free base into a salt or an amide of an optically active acid and regeneration of the amine after the usual separation of the diastereomeric mixture thus obtained.

It will also be understood that the optically active compounds of the present invention may be used either as a purified isomeric product obtained as a natural consequence of the reaction sequences described above or any reaction sequence for the preparation of the compounds which results in a mixed isomeric product containing the biologically active isomer or isomers.

The invention is further illustrated by th following Examples, without, however, being limited thereto.

EXAMPLE 1

Preparation of $N^2$-chloroacetylglycinanilide used as starting material a. Preparation of 2-chloro-N-phenylacetamide Aniline (93.1 g; 1.00 mole) was dissolved in toluene (750 ml), 10 % NaOH (750 ml) was added and the stirred mixture was cooled to 0°C. Chloroacetyl chloride (197 g; 1.75 mole) was added dropwise during 45 minutes while keeping the temperature below 10°C. Stirring was continued at room temperature for about one hour. The precipitated crystalline 2-chloro-N-phenylacetamide was filtered off, washed on the filter with cold toluene and dried in vacuo at 60°C. Yield: 151 g (90.0 %); m.p. 134°–136°C.

b. Preparation of glycinanilide

A solution of 2-chloro-N-phenylacetamide (50.0 g; 0.295 mole) in ethanol (1000 ml) was cooled to 0°C. The solution was saturated with ammonia (5 hours). Stirring was continued at room temperature for about 13 days. The solvent was removed under vacuum. The crystalline residue was taken up in 2N HCl and filtered. The filtrate was made alkaline by the addition of 5N $NH_3$. The alkaline phase was extracted three times with benzene-$CHCl_3$. The organic layer was dried over anhydrous $Na_2SO_4$ and the solvents were evaporated. The colourless oily residue crystallized by standing in the cold. The basic product was characterized by preparing the hydrochloride. Yield: 37.5 g (71.0 %) as glycineanilide. The hydrochloride melted at 175°–176°C (ethanol).

c. Preparation of $N^2$-chloroacetylglycineanilide

Glycineanilide (20.0 g; 0.108 mole) was dissolved in toluene (125 ml), 10 % NaOH (125 ml) was added and the stirred mixture was cooled to −5°C. Chloroacetyl chloride (21.3 g; 0.189 mole) was added dropwise during 15 minutes while keeping the temperature below 5°C. Stirring was continued at room temperature for about 1.5 hour. The crystalline precipitate was collected after centrifugation, was dried on a filter and finally in vacuo at 60°C. Yield on $N^2$-chloroacetylglycineanilide: 17.4 g (71.0 %); m.p. 174°–175°C (ethanol).

EXAMPLE 2

Preparation of N,N-diethylglycylglycine anilide

A solution of chloroacetylglycineanilide (10.0 g; 0.0443 mole) and diethylamine (9.7 g; 0.133 mole) in benzene (125 ml) was heated under reflux for 5 hours. The solution was cooled and diluted with ether (125 ml) whereby a crystalline mixture of diethylamine hydrochloride and N,N-diethylglycylglycineanilide (as base) was obtained. The mixture was shaken with cold water (2 × 100 ml) and the crystalline residue was recrystallized from water-isopropanol. The desired compound melted at 162°–164°C. Yield: 2.6 g (22.3 %).

EXAMPLE 3

Preparation of N,N-diethylglycylglycine-2,6-xylidide

A mixture of $N^2$-chloroacetylglycine-2,6-xylidide (15.0 g; 0.059 mole) and diethylamine (12.9 g; 0.177 mole) in benzene (300 ml) was heated under reflux (5 hours). The solution was cooled, diluted with absolute ether (300 ml) and the crystalline precipitate of diethylamine hydrochloride was filtered off. The filtrate was evaporated to dryness under vacuum. The light yellow residue was recrystallized in methanol (150 ml) whereby white needles were obtained, filtered off and washed on the filter with cold ether. The desired compound melted at 119°–121°C. Yield: 11.5 g (67.0 %).

The $N^2$-chloroacetylglycine-2,6-xylidide used as starting material was prepared in the following way.

a. Preparation of glycine-2,6-xylidide

A solution of 2-chloroaceto-2,6-xylidide (50.0 g; 0.253 mole) in ethanol (1000 ml) was cooled to 0°C. The solution was saturated with ammonia (5 hours). Stirring was continued at room temperature for about 6 days. The solvent was removed under vacuum. The white crystalline residue was dissolved in boiling isopropane-water(400 ml).

The solution was allowed to stand at room temperature over night whereby the glycine-2,6-xylidide hydrochloride crystallized as colourless needles. Yield: 27.8 g (51.5 %); m.p. 292°–293°C, (decomp.)

b. Preparation of $N^2$-chloroacetylglycine-2,6-xylidide

Glycine-2,6-xylidide hydrochloride (22.0 g; 0.103 mole) was dissolved in toluene (150 ml), 10 % NaOH (125 ml) was added and the stirred mixture was cooled to 0°C. Chloroacetyl chloride (20.3 g; 0.180 mole) was added dropwise during 15 minutes while keeping the temperature below 10°C. Stirring was continued at room temperature for about 2 hours. The white crystalline precipitate obtained was collected by centrifugation, sucked dry on a filter and was finally dried in vacuo at 60°C. Yield of $N^2$-chloracetylglycine-2,6-xylidide: 24.0 g (91.9 %).

EXAMPLE 4

Preparation of Glycylglycin-2,6-xylidide hydrochloride

A solution of $N^2$-chloroacetylglycine-2,6-xylidide (2.5 g; 0.0098 mole) (prepared according to Example 3) in ethanol (25 ml) and methanol (25 ml) was cooled to 0°C. The solution was saturated with ammonia (5 hours). Stirring was continued at room temperature for 7 days. The solvent was removed under vacuum. The light brown crystalline residue was recrystallized twice from isopropanol. The colourless crystals obtained was washed on the filter with absolute ether and dried in vacuo at 60°C. The desired compound melted at 252°–255°C. Yield: 250 mg (10.7 %).

EXAMPLE 5

Preparation of N-Propylglycylglycine-2,6-xylidide hydrochloride

A mixture of $N^2$-chloroacetylglycine-2,6-xylidide (5.0 g; 0.0197 mole) (see Example 3) and n-propylamine (3,5 g; 0.0590 mole) in benzene (50 ml) was heated under reflux (5 hours). The solution was cooled, diluted with ether (50 ml) and the crystalline precipitate of n-propylamine hydrochloride was filtered off. The filtrate was evaporated to dryness under vacuum. The yellow oily residue was dissolved in acetone (50 ml) and absolute ether (50 ml) whereafter a 3N solution of hydrogen chloride in ether (1.5 mole) was added dropwise while stirring and cooling the solution at 0°C. The crude crystals obtained was recrystallized from isopropanol-water and the pure desired compound was washed on the filter with absolute ether and dried in vacuo at 60°C. Yield: 2.7 g (23.0 %); m.p. 214°–215°C.

EXAMPLE 6

Preparation of $N^3,N^3$-diethyl-$N^1$-($\alpha,\alpha$-dimethylbenzyl) glycylglycine amide A mixture of $N^2$-chloroacetyl-$N^1$-($\alpha,\alpha$-dimethylbenzyl)glycine amide (2,9 g; 0.0108 mole) and diethylamine (4.4 g; 0.0604 mole) in benzene (85 ml) was heated under reflux for 8 hours. The solution was cooled, diluted with absolute ether (85 ml) and the crystalline precipitate of diethylamine hydrochloride was filtered off. The filtrate was extracted three times with 2N HCl, the aqueous phase was washed with ether and made alkaline with 10N NaOH. The alkaline phase was extracted three times with ether, the ethereal layer was dried over anhydrous $Na_2SO_4$; filtered and treated with carbon black. After evaporation of the ether and several recrystallizations of the residue from isopropylether the $N^3,N^3$-diethyl-$N^1$-($\alpha,\alpha$-dimethylbenzyl)glycylglycineamide was obtained as a white compound which melted at 87°–89°C. Yield: 1.1 g (33.3 %).

The $N^2$-chloroacetyl-$N^1$-($\alpha,\alpha$-dimethylbenzyl)-glycineamide used as starting material was prepared in the following way.

a. Preparation of 2-chloro-N-($\alpha,\alpha$-dimethylbenzyl)-acetamide $\alpha,\alpha$-dimethylbenzylamine hydrobromide (19.9 g; 0.092 mole) was suspended in toluene (100 ml) and 10 % NaOH (140 ml) was added while stirring at 0°C. Chloroacetyl chloride (18.3 g; 0.162 mole) was added dropwise during 5 minutes while keeping the temperature below 15°C. Stirring was continued at room temperature for about 3 hours. The precipitated crystalline 2-chloro-N-($\alpha,\alpha$-dimethylbenzyl)acetamide was filtered off, washed on the filter with cold toluene and dried in vacuo at 50°C. The alkaline phase was separated and extracted with toluene. The combined toluene solutions were washed with water and dried over anhydrous $Na_2SO_4$. When the toluene was evaporated a second crop of the crystalline 2-chloro-N-($\alpha,\alpha$-dimethylbenzyl)-acetamine was obtained. Total yield: 17.8 g (91.5 %); m.p. 86°–88°C.

b. Preparation of $N^1$-($\alpha,\alpha$-dimethylbenzyl)glycineamide

A solution of 2-chloro-N-($\alpha,\alpha$-dimethylbenzyl)-acetamide (11.5 g; 0.054 mole) in ethanol (300 ml) was cooled to 0°C. The solution was saturated with ammonia (5 hours). Stirring was continued at room temperature for about 6 days. The solvent was removed under vacuum. The oily residue was taken up in 2N HCl and filtered. The filtrate was made alkaline by the addition of 2N NaOH. The alkaline phase was extracted three times with ether. The organic layer was dried over, anhydrous $Na_2SO_4$ and the solvent was evaporated. The $N^1$-($\alpha,\alpha$-dimethylbenzyl)glycineamide was obtained as a light brown oil. Yield: 6.5 g (62.5 %).

c. Preparation of $N^2$-chloroacetyl-$N^1$-($\alpha,\alpha$-dimethylbenzyl)glycineamide N-($\alpha,\alpha$-dimethylbenzyl)glycineamide (6.0 g; 0.031 mole) was dissolved in benzene (60 ml), 10 % NaOH (30 ml) was added and the stirred mixture was cooled to 0°C. Chloroacetyl chloride (6.2 g; 0.055 mole) was added dropwise during 10 minutes while keeping the temperature below 15°C. Stirring was continued at 0°C for 3 hours. The light brown crystalline precipitate was filtered off and dried in vacuo at 50°C. Yield of $N^2$-chloroacetyl-$N^1$-($\alpha,\alpha$-dimethylbenzyl)glycineamide: 3.0 g (35 %); m.p. 94°–97°C.

EXAMPLE 7

Preparation of $N^3,N^3$-diethyl-$N^1$-($\alpha,\alpha$-dimethylbenzyl)glycylalanineamide A mixture of $N^2$-chloroacetyl-$N^1$-($\alpha,\alpha$-dimethylbenzyl)alanineamide (8.6 g; 0.030 mole) and diethylamine (12.4 g; 0.170 mole) in benzene (140 ml) was heated under reflux for 7 hours. The solution was cooled, diluted with absolute ether (140 ml) and the crystalline precipitate of diethylamine hydrochloride was filtered off. The filtrate was extracted three times with 2N HCl, the aqueous phase was washed with ether and made alkaline with 10N NaOH. The alkaline phase was extracted three times with ether and the ethereal phase was dried over anhydrous $Na_2SO_4$. After evaporation of the ether and several recrystallizations of the residue from hexane under treatment of the solutions with carbon black the $N^3,N^3$-diethyl-$N^1$-($\alpha,\alpha$-dimethylbenzyl)glycylalanineamide was obtained as a white compound which melted at 78°–79°C. Yield: 5.0 g (51.5 %).

The $N^2$-chloroacetyl-$N^1$-($\alpha,\alpha$-dimethylbenzyl)alanineamide used as starting material was prepared in the following way.

a. Preparation of 2-bromo-N-($\alpha,\alpha$-dimethylbenzyl)-propionamide $\alpha,\alpha$-dimethylbenzylamine (27.0 g; 0.200 mole) was dissolved in toluene (200 ml), 10 % NaOH (200 ml) was added and the stirred mixture was cooled to 0°C. Bromopropionyl bromide (76.0 g; 0.352 mole) was added dropwise during 30 minutes while keeping the temperature below 10°C. Stirring was continued at room temperature for about 3 hours. The precipitated crystalline 2-bromo-N-($\alpha,\alpha$-dimethylbenzyl)propionamide was filtered off, washed on the filter with cold toluene and dried in vacuo at 60°C. Yield: 45.2 g (83.8 %); m.p. 102°–103°C.

b. Preparation of $N^1$-($\alpha,\alpha$-dimethylbenzyl)alanineamide

A solution of 2-bromo-N-($\alpha,\alpha$-dimethylbenzyl)propionamide (24.0 g; 0.088 mole) in ethanol (500 ml) was cooled to 0°C. The solution was saturated with ammonia (5 hours). Stirring was continued at room temperature for about 7 days. The solvent was removed under vacuum. The oily residue was taken up in benzene. The benzene phase was extracted with 5N HCl. The aqueous phase was washed with ether, made alkaline with 5N NaOH, saturated with NaCl and extracted several times with benzene. The benzene solution was dried over anhydrous $Na_1SO_4$ and the solvent was evaporated. The $N^1$-($\alpha,\alpha$-dimethylbenzyl)alanineamide was obtained as an almost colourless oil. Yield: 14.6 g (79.8 %).

c. Preparation of $N^2$-chloroacetyl-$N^1$-($\alpha,\alpha$-dimethylbenzyl)alanineamide $N^1$-($\alpha,\alpha$-dimethylbenzyl)alanineamide (7.2 g; 0.035 mole) was dissolved in benzene (70 ml), 10 % NaOH (35 ml) was added and the stirred mixture was cooled to 0°C. Chloroacetyl chloride (6.8 g; 0.061 mole) was added dropwise during 10 minutes while keeping the temperature below 10°C. Stirring was continued at 10°C for 2 hours. The white crystalline precipitate was filtered off, washed with cold benzene and cold water and dried in vacuo at 40°C. Yield of $N^2$-chloroacetyl-$N^1$-($\alpha,\alpha$-dimethylbenzyl)alanineamide: 8.8 g (89.8 %); m.p. 151°–153°C.

EXAMPLE 8

Preparation of $N^3,N^3$-diethyl-$N^1$-($\alpha,\alpha$-dimethylbenzyl)alanylalanineamide A mixture of $N^2$-(2-bromopropionyl)-$N^1$-($\alpha,\alpha$-dimethylbenzyl)alanineamide (9.1 g; 0.027 mole) and diethylamine (11.0 g; 0.150 mole) in benzene (110 ml) was heated under reflux for 7 hours. The solution was cooled, diluted with absolute ether (110 ml) and filtered. The filtrate was extracted three times with 2N HCl, the aqueous phase was washed with ether and made alkaline with 10N NaOH whereby an oil was obtained that soon crystallized. Several recrystallizations from hexane under treatment of the solutions with carbon black afforded white crystals of $N^3,N^3$-diethyl-$N^1$-($\alpha,\alpha$-dimethylbenzyl)alanylalanineamide which melted at 92°–93°C. Yield: 5.8 g (65.2 %).

The $N^2$-(2-bromopropionyl)-$N^1$-($\alpha,\alpha$-dimethylbenzyl)alanineamide used as starting material was prepared in the following way.

$N^1$-($\alpha,\alpha$-dimethylbenzyl)alanineamide (7.2 g; 0.035 mole) (prepared according to Example 7) was dissolved in benzene (70 ml), 10 % NaOH (35 ml) was added and the stirred mixture was cooled to 0°C. Bromopropionyl bromide (13.2 g; 0.061 mole) was added dropwise during 10 minutes while keeping the temperature below 10°C. Stirring was continued at 10°C for 2 hours. The white crystalline precipitate was filtered off, washed with cold benzene and cold water and dried in vacuo at 40°C. Yield of $N^2$-(2-bromopropionyl)-N¹-(α,α-dimethylbenzyl)alanineamide: 9.3 g (78.2 %); m.p. 144°–146°C.

EXAMPLE 9

Preparation of Glycylglycine - 2,6-xylidide hydrochloride

To a solution of N²-chloroacetylglycine-2,6-xylidide (30.0 g; 0.118 mole) (prepared according to Example 3) in dimethylformamide (350 ml) was added potassium phthalimide (24.1 g; 0.130 mole) in portions during 5 minutes while stirring. Continued stirring and careful heating to 80°C brought the phthalimide salt into solution and the compounds were allowed to react for 2 hours at that temperature and finally for 1 hour at reflux temperature (146°–153°C) After distilling off 200 ml of dimethylformamide, glacial acetic acid (40 ml) and water (100 ml) were added to the residue and the mixture was stirred vigorously and warmed at about 100°C for 1.5 h. The mixture was cooled and the crude phthalimido derivative was filtered off, washed on the filter with cold water and dried in vacuo at 110°C.

The crude phthalimido derivative (27.9 g, 0.0764 mole) was mixed with 95 % ethanol (250 ml) and 85 % hydrazine hydrate (9.0 g, 0.1528 mole). The mixture was heated to reflux during vigorous stirring. In 15 minutes the phthalimido compound was almost completely dissolved and an intermediate compound began to form a thick precipitate which was made thinner by adding ethanol (150 ml) After 1 hour concentrated HCl (16 ml) was added and reflux was continued while stirring for a further 2.5 hours. The mixture was cooled and filtered. The residual precipitate was boiled with water and filtered off affording phthalimido hydrazide (11.9 g, 90.3 %). The combined filtrates were evaporated and the residue was recrystallized from acetone-water affording the desired compound. Yield: 16.9 g (81.6 %); m.p. 251°–253°C (cf. Example 4).

EXAMPLE 10

Preparation of N,N-diethylalanylglycine-2,6-xylidide

A mixture of N-²(2-bromopropionyl) glycine-2,6-xylidide (35.5 g, 0.113 mole) and diethylamine (46.5 g, 0.635 mole) in benzene (600 ml) was heated under reflux for (7 hours). The solution was evaporated to half the original volume, cooled, diluted with absolute ether (300 ml) and the crystalline precipitate of diethylamine hydrobromide was filtered off. The filtrate was extracted with 2N HCl and the aqueous phase was made alkaline with 2N NaOH while stirring and cooling. The white crystalline precipitate formed was filtered off, washed with water, recrystallized from acetone water (1:1) and ethanol-isopropyl ether (1:15) and dried in vacuo. Yield: 24.2 g (70.1 %); m.p. 117°–118°C.

a. Preparation of N²-(2-bromopropionyl) glycine-2,6-xylidide

Glycine-2,6-xylidide hydrochloride (32.8 g, 0.152 mole) was dissolved in benzene (325 ml), 10 % NaOH (250 ml) was added and the stirred mixture was cooled to 5°C. Bromopropionyl bromide (58.2 g, 0.270 mole) was added dropwise during 10 minutes while keeping the temperature below 20°C. Stirring was continued for about 2 hours at 10°C. The white crystalline precipitate was filtered off, washed on the filter with cold benzene and cold water and dried overnight at 100°C/30mm Hg. Yield: 43.0 g (90.5 %); m.p. 179°–184°C (decomp.).

EXAMPLE 11

Preparation of N,N-diethylglycylglycine-2-chloro-6-toluidide

A mixture of N²-chloroacetylglycine-2-chloro-6-toluidide (5.5 g, 0.020 mole) and diethylamine (8.2 g, 0.112 mole) in benzene (150 ml) was heated under reflux for 6.5 hours. Working up in analogy with Example 10 afforded the desired compound as a white crystalline substance melting at 104°–105°C/from aceton-water (1:1)/. Yield: 4.0 g (64.5 %).

a. Preparation of N²-chloroacetylglycine-2-chloro-6-toluidide

This compound was prepared from glycine-2-chloro-6-toluidide hydrochloride (14.0 g, 0.0596 mole) and chloroacetylchloride (11.9 g, 0.105 mole) in analogy with Example 3b. Yield: 12.1 g (74.0 %); m.p. 193°–195°C.

The compounds of the formula I which are exemplified in the foregoing Examples 2 through 8 have the following structural formulas and code numbers:

| Compound according to Example No. | Code | Structural formula |
|---|---|---|
| 2 | GEA 984 | 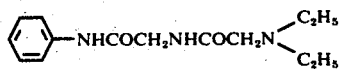 |
| 3 | GEA 968 | 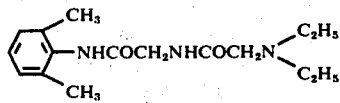 |
| 4 | GEA 986 | 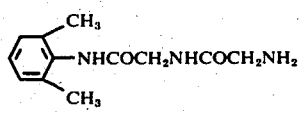 |
| 5 | GEA 988 |  |

-continued

| Compound according to Example No. | Code | Structural formula |
|---|---|---|
| 6 | GEA 980 | Ph-C(CH₃)(CH₃)-NHCOCH₂NHCOCH₂N(C₂H₅)₂ |
| 7 | GEA 981 | Ph-C(CH₃)(CH₃)-NHCOCH(CH₃)NHCOCH₂N(C₂H₅)₂ |
| 8 | GEA 982 | Ph-C(CH₃)(CH₃)-NHCOCH(CH₃)NHCOCH(CH₃)N(C₂H₅)₂ |

BIOLOGICAL TESTS

The ability of compounds according to the invention to suppress cardiac arrhythmias in mammals has been demonstrated. For comparison tests were also carried out on lidocaine,

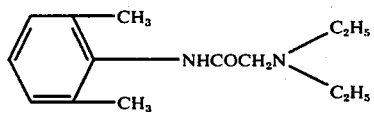

The ability of the compounds to suppress cardiac arrhythmias has been demonstrated in mice and guinea-pigs.

The method used in mice was essentially the same as described by Lawson (J. Pham. Exp. Therap. 160, 22 (1968). Male mice (NMRI, 17–25 g) were used. Unanesthetized, untreated mice show cardiac ventricular fibrillation upon exposure to chloroform vapor. The ventricular fibrillation is abolished if the animals are pretreated with appropriate doses of known antiarrhythmic agents before exposure to chloroform.

For determination of acute toxicity groups of 10 mice were treated orally with varying doses of compound observing the incidence of death, during a 7 days period. LD50 and LD 0.1 were calculated by means of a logarithmic-probit graph paper.

For determination of antiarrhythmic effect groups of 10 mice were pretreated by the oral route with varying sublethal doses of compound 10 to 300 min. respectively before being placed individually in a beaker containing chloroform. The mouse was removed from the beaker at the time of respiratory arrest and the thorax opened. Examination of ventricular fibrillation was made by means of ECG-recordings (lead II). The effect of the compound was expressed as the number of animals in per cent which were protected from fibrillation.

As is seen from table 1 the compounds displayed a good antiarrhythmic effect in this test.

Table 1

Acute oral toxicity (LD50) and antifibrillatory effects in mice

| Compound (Code number) | Toxicity LD50 p.o. mg/kg bodyweight | Dose of test compound p.o. mg/kg bodyweight | Protection against ventricular fibrillation Percentage animals protected from fibrillation at a time interval between pretreatment and chloroform vapor of | | |
|---|---|---|---|---|---|
| | | | 10 | 60 | 300 min |
| GEA 980 | >500[a] | 100 | 11 | 10 | |
| GEA 980 | | 300 | 25 | 10 | |
| GEA 980 | | 500 | 65 | 0 | |
| GEA 981 | 880 | 88[1] | 35 | 10 | |
| GEA 981 | | 610[2] | 90 | 45 | |
| GEA 982 | 660 | 66[1] | 0 | 0 | |
| GEA 982 | | 210[2] | 40 | 15 | |
| GEA 984 | >1000[a] | 250 | 0 | 0 | |
| GEA 984 | | 500 | 70 | 10 | |
| GEA 984 | | 1000 | 75 | 0 | |
| GEA 968 | 535 | 54[1] | 45 | 55 | 15 |
| GEA 968 | | 100 | 70 | 65 | 45 |
| GEA 968 | | 250[2] | 90 | 90 | 70 |
| Lidocaine | 445 | 45[1] | 30 | 10 | |
| | | 150[2] | 70 | 20 | |

Notes:
[a]:LD50 not determined. The compound obviously has a very low toxicity
[1]:One tenth of the dose which kills 50 % of the animals
[2]:LD 0.1 (the dose which kills 0.1 % of the animals)

Some of the compounds were tested for protection against aconitine-induced arrhythmias in the guinea-pig.

The procedure used by Vargaftig et al. (Eur. J. Pharmacol. 6, 49, 1969) was slightly modified; Guinea-pigs of both sexes (250–400 g) were anaesthetized with uretane (1 g/kg bodyweight, i.p.). A plastic tube was introduced into the trachea and a thin plastic catheter into the jugular vein. Respiration was supported by means of a Harward Rodent Respirator 680. Aconitine was infused i.v. at a rate of 3 µg/min by means of a Palmer slow injection apparatus. The ECG (lead II) was continuously monitored. The amount of aconitine (μg/kg bodyweight) injected to induce ventricular tachycardia, fibrillation and asystolie was calculated. Test compounds were given i.p. with different time intervals between injection of drug and start of aconitine infusion. A protective effect is demonstrated in that the toxic effects of aconitine are delayed, i.e. more aconitine is needed to cause arrhythmia. Table 2 demonstrates the effects of some of the new compounds in comparison with lidocaine in this test.

Table 2

| Compound | Time between pretreatment with test compound and start of aconitine infusion min | Dose of test compound i.p. mg/kg bodyweight | Dose of aconitine (μg/kg bodyweight) necessary for development of ECG-changes indicating | | |
|---|---|---|---|---|---|
| | | | Tachycardia | Fibrillation | Asystolie |
| Control (no drug) | 15 | — | 84 ± 3 | 166 ± 17 | 224 ± 20 |
| GEA 984 | 15 | 100 | 95 ± 9 | 211 ± 18 | 284 ± 29 |
| GEA 968 | 15 | 25 | 91 ± 6 | 155 ± 10 | 210 ± 12 |
| GEA 968 | 15 | 50 | 161 ± 15 | 284 ± 25 | 378 ± 33 |
| GEA 968 | 15 | 100 | 225 ± 35 | 356 ± 32 | 632 ± 132 |
| Lidocaine | 15 | 25 | 66 ± 7 | 176 ± 12 | 237 ± 35 |

Note:
6–8 animals were used in each test. Test results are given as mean values ± standard error of the means.

The results show that the new compounds were effective in this test. GEA 968 which could be given in higher doses than lidocaine because of lower toxicity was markedly potent.

It is seen from the biological tests described above that the tested compounds according to the invention exhibit valuable antiarrhythmic effects. In particular the compound with code number GEA 968 exhibits good antiarrhythmic effects in both the test methods used, and the duration of effectiveness of this compound is especially significant.

The animal tests described above did not include quantitative evaluation of side effects. However, it was qualitatively observed that the side effects of the compounds of the present invention appeared to be less significant. This was especially true of compound GEA 968 which gave some preliminary indication of actually improving the contractility of the heart.

The effects of intravenous infusion of GEA968 was also studies on two unanesthesized dogs with ventricular arrhythmias produced by coronary artery ligation, essentially following the procedure of A. S. Harris, Circulation, Vol. I, page 1318 (1950). The two dogs with well-developed arrhythmias received a constant infusion of 0.5 mg/kg/min. of GEA968. This treatment resulted in a suppression of the arrhythmias, and the suppression was observed for an unusually long duration.

We claim:
1. A pharmaceutical preparation for treating cardiac arrythmias containing as an active substance in an amount effective to treat symptoms of cardiac arrythmias, a compound having the structural formula

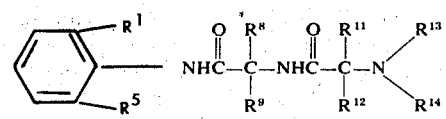

or a pharmaceutically acceptable acid addition salt thereof, wherein $R^1$ and $R^5$ are the same or different and selected from the group consisting of hydrogen, methyl, and halogen; $R^8$, $R^9$, $R^{11}$ and $R^{12}$ are the same or different and selected from the group consisting of hydrogen and methyl; $R^{13}$ and $R^{14}$ are the same or different and selected from the group consisting of hydrogen and lower alkyl radicals having from 1 to 3 carbon atoms, together with a pharmaceutically acceptable carrier.

2. A pharmaceutical preparation according to claim 1, wherein said compound is

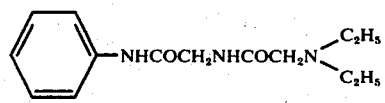

or a pharmaceutically acceptable acid addition salt thereof.

3. A pharmaceutical preparation according to claim 1, wherein said compound is

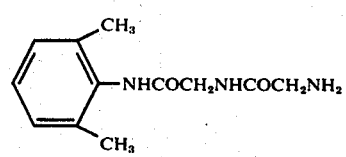

or a pharmaceutically acceptable acid addition salt thereof.

4. A pharmaceutical preparation according to claim 1, wherein said compound is

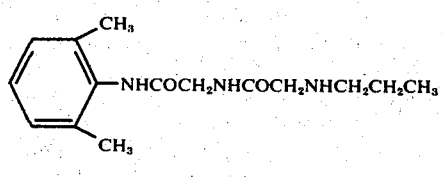

or a pharmaceutically acceptable acid addition salt thereof.

5. A pharmaceutical preparation according to claim 1 wherein said compound is

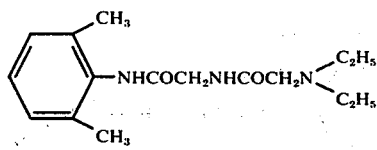

or a pharmaceutically acceptable acid addition salt thereof.

6. A pharmaceutical preparation for treating cardiac arrythmias containing as an active substance in an amount effective to treat symptoms of cardiac arrythmias a compound having the structural formula

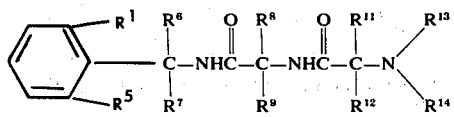

or a pharmaceutically acceptable acid addition salt thereof, wherein $R^1$ and $R^5$ are the same or different and selected from the group consisting of hydrogen, methyl, and halogen; $R^6$, $R^7$, $R^8$, $R^9$, $R^{11}$ and $R^{12}$ are the same or different and selected from the group consisting of hydrogen and methyl; $R^{13}$ and $R^{14}$ are the same or different and selected from the group consisting of hydrogen and lower alkyl radicals having from 1 to 3 carbon atoms, together with a pharmaceutically acceptable carrier.

7. A pharmaceutical preparation according to claim 6, wherein said compound is

or a pharmaceutically acceptable acid addition salt thereof.

8. A pharmaceutical preparation according to claim 6, wherein said compound is

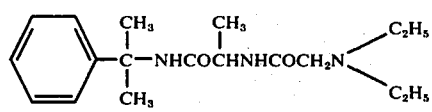

or a pharmaceutically acceptable acid addition salt thereof.

9. A pharmaceutical preparation according to claim 6, wherein said compound is

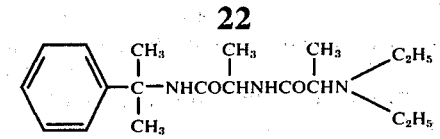

or a pharmaceutically acceptable acid addition salt thereof.

10. A method for treating cardiac arrythmias in mammals characterized by the administration to a subject suffering from symptoms of cardiac arrythmias of a compound having the structural formula

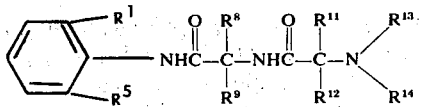

or a pharmaceutically acceptable acid addition salt thereof, wherein $R^1$ and $R^5$ are the same or different and selected from the group consisting of hydrogen, methyl, and halogen; $R^8$, $R^9$, $R^{11}$ and $R^{12}$ are the same or different and selected from the group consisting of hydrogen and methyl; $R^{13}$ and $R^{14}$ are the same or different and selected from the group consisting of hydrogen and lower alkyl radicals having from 1 to 3 carbon atoms; in an amount effective to mitigate said symptoms.

11. A method according to claim 10, wherein said compound is

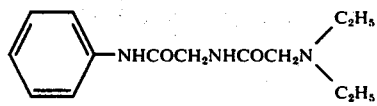

or a pharmaceutically acceptable acid addition salt thereof.

12. A method according to claim 10, wherein said compound is

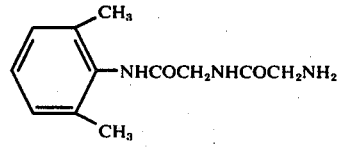

or a pharmaceutically acceptable acid addition salt thereof.

13. A method according to claim 10, wherein said compound is

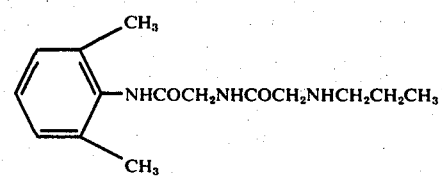

or a pharmaceutically acceptable acid addition salt thereof.

14. A method according to claim 10 wherein said compound is

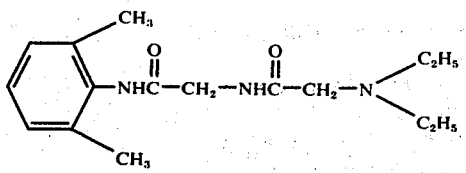

or a pharmaceutically acceptable acid addition salt thereof.

15. A method for treating cardiac arrythmias in mammals characterized by the administration to a subject suffering from symptoms of cardiac arrythmias of a compound having the structural formula

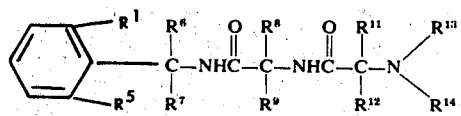

or a pharmaceutically acceptable acid addition salt thereof, wherein $R^1$ and $R^5$ are the same or different and selected from the group consisting of hydrogen, methyl, and halogen; $R^6$, $R^7$, $R^8$, $R^9$, $R^{11}$ and $R^{12}$ are the same or different and selected from the group consisting of hydrogen and methyl; $R^{13}$ and $R^{14}$ are the same or different and selected from the group consisting of hydrogen and lower alkyl radicals having from 1 to 3 carbon atoms; in an amount effective to mitigate said symptoms.

16. A method according to claim 15, wherein said compound is

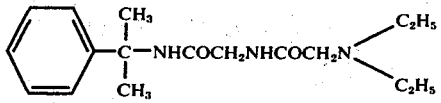

or a pharmaceutically acceptable acid addition salt thereof.

17. A method according to claim 15, wherein said compound is

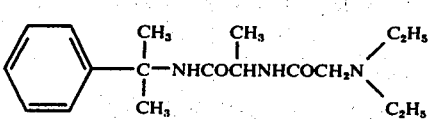

or a pharmaceutically acceptable acid addition salt thereof.

18. A method according to claim 15, wherein said compound is

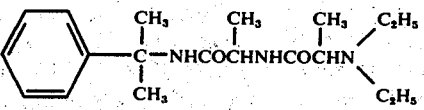

or a pharmaceutically acceptable acid addition salt thereof.

* * * * *